United States Patent
Rockrohr

(10) Patent No.: US 7,998,118 B2
(45) Date of Patent: Aug. 16, 2011

(54) PISTON SEAL FOR SINGLE INCISION SURGERY

(75) Inventor: Brian Rockrohr, Waterbury, CT (US)

(73) Assignee: Tyco Healthcare Group LP, New Haven, CT (US)

( * ) Notice: Subject to any disclaimer, the term of this patent is extended or adjusted under 35 U.S.C. 154(b) by 111 days.

(21) Appl. No.: 12/481,833

(22) Filed: Jun. 10, 2009

(65) Prior Publication Data

US 2010/0016800 A1 Jan. 21, 2010

Related U.S. Application Data

(60) Provisional application No. 61/081,473, filed on Jul. 17, 2008.

(51) Int. Cl.
*A61M 5/178* (2006.01)

(52) U.S. Cl. .................................. 604/167.06

(58) Field of Classification Search ............. 604/164.01, 604/167.01, 167.02, 167.03, 167.06, 158; 251/251, 4, 213, 294; 606/108
See application file for complete search history.

(56) References Cited

U.S. PATENT DOCUMENTS

| | | | |
|---|---|---|---|
| 4,092,010 A | 5/1978 | Carlson, Jr. | |
| 4,513,948 A * | 4/1985 | Konig | 251/212 |
| 4,679,557 A | 7/1987 | Opie et al. | |
| 5,209,737 A | 5/1993 | Ritchart et al. | |
| 5,279,593 A | 1/1994 | Hiltebrandt | |
| 5,308,336 A | 5/1994 | Hart et al. | |
| 5,391,153 A | 2/1995 | Haber et al. | |
| 5,407,433 A | 4/1995 | Loomas | |
| 5,411,483 A | 5/1995 | Loomas et al. | |
| 5,634,908 A * | 6/1997 | Loomas | 604/167.06 |
| 5,820,600 A | 10/1998 | Carlson et al. | |
| 7,025,747 B2 | 4/2006 | Smith | |
| 2004/0064100 A1 | 4/2004 | Smith | |
| 2004/0215209 A1 | 10/2004 | Almond et al. | |
| 2006/0020281 A1 | 1/2006 | Smith | |
| 2008/0319396 A1 | 12/2008 | Smith | |

FOREIGN PATENT DOCUMENTS

| | | |
|---|---|---|
| DE | 19941594 | 3/2001 |
| EP | 0550069 | 7/1993 |
| WO | WO 97/42991 | 11/1997 |
| WO | WO 99/29250 | 6/1999 |

OTHER PUBLICATIONS

European Search Report for corresponding EP 09251812 date of mailing is Oct. 19, 2009 (3 pages).

* cited by examiner

*Primary Examiner* — Christopher D Koharski

(57) ABSTRACT

A surgical portal apparatus for use during a minimally invasive procedure includes a housing and a portal member extending distally from the housing. The housing and portal member combination defines a longitudinal axis. The portal member is sized to be positioned within tissue and has an opening at the distal end. The apparatus also has a pliable seal and a plurality of concentrically arranged piston members, disposed within the housing. The pistons are engageable with the pliable seal and are adapted for moving relative to the housing to control the diameter of a passage through the inner portion of the seal in response to the insertion of a surgical object.

16 Claims, 7 Drawing Sheets

PISTON SEAL FOR SINGLE INCISION SURGERY

CROSS REFERENCE TO RELATED APPLICATION

The present application claims the benefit of and priority to U.S. Provisional Application Ser. No. 61/081,473 filed on Jul. 17, 2008, the entire contents of which are incorporated herein by reference.

BACKGROUND

1. Technical Field

The present disclosure relates to a device, and a method of use thereof, for facilitating access to a patient's internal cavities during a surgical procedure. More particularly, the present disclosure relates to a surgical apparatus adapted for insertion into an incision in tissue, and for the sealed reception of one or more surgical objects, so as to form a substantially fluid-tight seal with both the tissue and the surgical object, or objects.

2. Background of the Related Art

Today, many surgical procedures are performed through small incisions in the skin, as compared to the larger incisions typically required in traditional procedures, in an effort to reduce trauma to the patient and recovery time. Generally, such procedures are referred to as "endoscopic", unless performed on the patient's abdomen, in which case the procedure is referred to as "laparoscopic". Throughout the present disclosure, the term "minimally invasive" should be understood to encompass both endoscopic and laparoscopic procedures. During a typical minimally invasive procedure, surgical objects, such as surgical access devices, e.g., trocar and trocar assemblies, or endoscopes, are inserted into the patient's body through one or more incisions in tissue.

In general, prior to the introduction of the surgical object into the patient's body, insufflation gasses are used to enlarge the area surrounding the target surgical site to create a larger, more accessible work area. Accordingly, the maintenance of a substantially fluid-tight seal about the surgical object, or objects, is important, so as to prevent the escape of the insufflation gases and the deflation or collapse of the enlarged surgical work area.

To this end, various apparatus, including valves, seals and the like, are used during the course of minimally invasive procedures and are widely known in the art. However, a continuing need exists for an apparatus and associated seal for insertion in tissue that can accommodate a variety of differently sized surgical objects while maintaining the integrity of an insufflated workspace.

SUMMARY

Accordingly, the present disclosure provides a surgical portal apparatus with a seal assembly, which will allow a surgeon to efficaciously utilize instruments of varying diameter in a surgical procedure. The surgical portal apparatus includes a longitudinal opening to permit passage of a surgical object through the surgical portal apparatus. This seal assembly obviates the need for multiple adapters to accommodate instruments of varying diameters by providing a seal with an adjustable opening. One embodiment is directed to a surgical portal apparatus having a housing, a portal member, a pliable seal, and a plurality of concentrically arranged pistons for use within the housing. The portal member extends from the housing, having a longitudinal axis defined therethrough. The portal member is dimensioned for positioning within tissue and defining an opening at a distal end. The piston members are engageable with the inner portions of the pliable seal and are adapted for movement relative to the housing to automatically control the diameter of the passage in response to insertion of a surgical instrument.

Each of the plurality of piston members acts upon the inner portions of a pliable seal. Each of the plurality of piston members is retained in a respective channel within the housing. The channels are configured to restrict movement of piston members in a radial direction. As the plurality of piston members are moved toward the center of the passage, the dimensioning of the passage is reduced. Each of the plurality of piston members is capable of moving independently of each other. The seal is fully open in the "at rest" position and is capable of fully closing to prevent the escape of fluid when activated. A duck-bill seal or zero seal may be used in conjunction to aid in preventing the escape of fluid during insertion and extraction of a surgical object.

The piston members are movable in response to the introduction of a surgical object to establish a substantial sealing relationship with the surgical object. Movement is accomplished by an actuation mechanism acting upon the piston members, which in turn act against the pliable seal to decrease the diameter of the passage. The actuation mechanism includes a motor with resistive circuitry. The resistive circuitry is configured to detect an increased load on the motor and stops the motor when a specific load is detected. The motor releasably holds the load torque on the piston members in the second relative position causing a constant seal with the surgical object.

The surgical portal apparatus includes a sensor positioned within the housing. Located distal to the piston seal, the sensor adapted to be engaged by the surgical object during introduction of the surgical object within the housing. Engagement of the sensor activates the motor and thereby causes the movement of the piston members of the piston seal, from the first relative position to the second relative position. The sensor is capable of determining location and size of the inserted surgical object and moves the plurality of piston members accordingly.

In another embodiment, the surgical portal apparatus includes a manual actuation mechanism mounted to the housing and operatively connected to the plurality of piston members of the piston seal. A clinician engages and manipulates the manual actuation mechanism to selectively move the plurality of piston members between the first and second relative positions. In still another embodiment, the actuation mechanism includes an electromagnetic repulsion system capable of moving the plurality of piston members.

BRIEF DESCRIPTION OF THE DRAWINGS

The accompanying drawings, which are incorporated in and constitute a part of this specification, illustrate embodiments of the disclosure, and together with a general description of the disclosure given above, and the detailed description of the embodiments given below, serve to explain the principles of the disclosure.

Other features and advantages of the present disclosure will become apparent from the following detailed description, taken in conjunction with the accompanying drawings, which illustrate, by way of example, the principals of the present disclosure.

DETAILED DESCRIPTION

The seal assembly of the present disclosure provides a substantial seal between a body cavity of a patient and the outside atmosphere before, during, and after insertion of an instrument through a trocar assembly. Moreover by providing a fluid tight seal with each instrument when inserted, the seal assembly of the present disclosure is capable of accommodating instruments of varying diameters, e.g., from about 5 mm to about 15 mm. The flexibility of the present seal assembly greatly facilitates endoscopic surgery especially wherein a variety of instruments having differing diameters are often interchanged during a single surgical procedure.

The seal assembly contemplates the introduction and manipulation of various types of instrumentation, adapted for insertion through a trocar and/or trocar assembly, while maintaining a fluid tight interface about the instrumentation to preserve the atmospheric integrity of a surgical cavity from a gas and/or fluid leakage. Specifically, the presently disclosed seal assembly substantively eliminates introduction and removal forces upon a surgical object relative to the seal housing axis and automatically adjusts the seal to compensate for off-center movement of the implement relative to the housing thereby minimizing contamination and leakage from the body cavity. Examples of instrumentation contemplated for use with the present disclosure include clip appliers, graspers, dissectors, retractors, staplers, laser probes, photographic devices, endoscopes and laparoscopes, tubes, and the like. Such instruments will be collectively referred to herein as "surgical objects".

Figure 1:
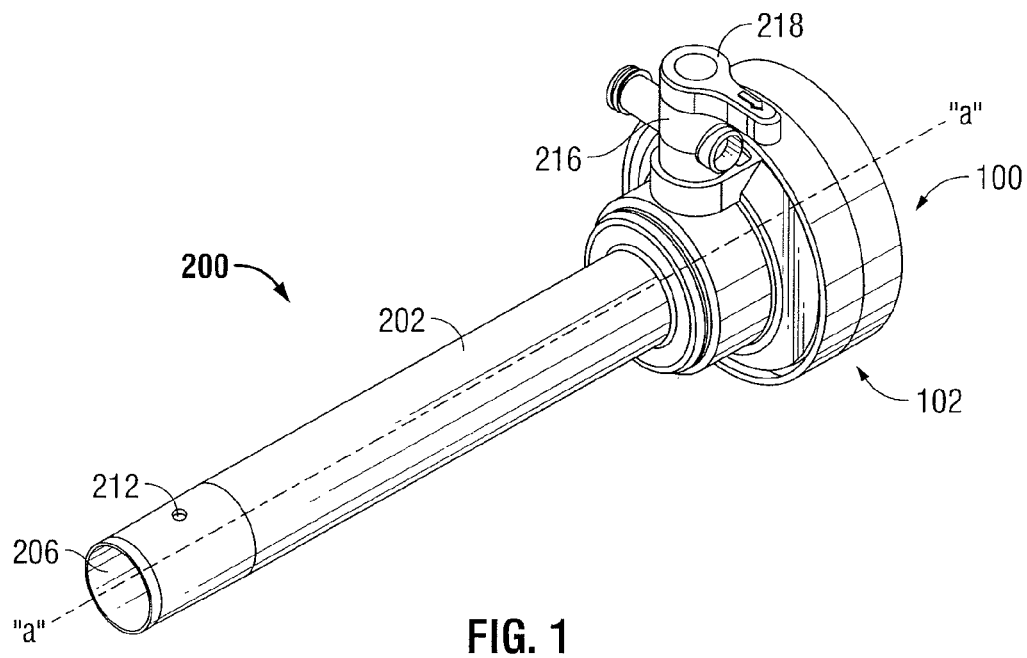
FIG. 1 is a right, perspective view of a trocar assembly and a seal assembly in accordance with the principles of the present disclosure.
Figure 2:
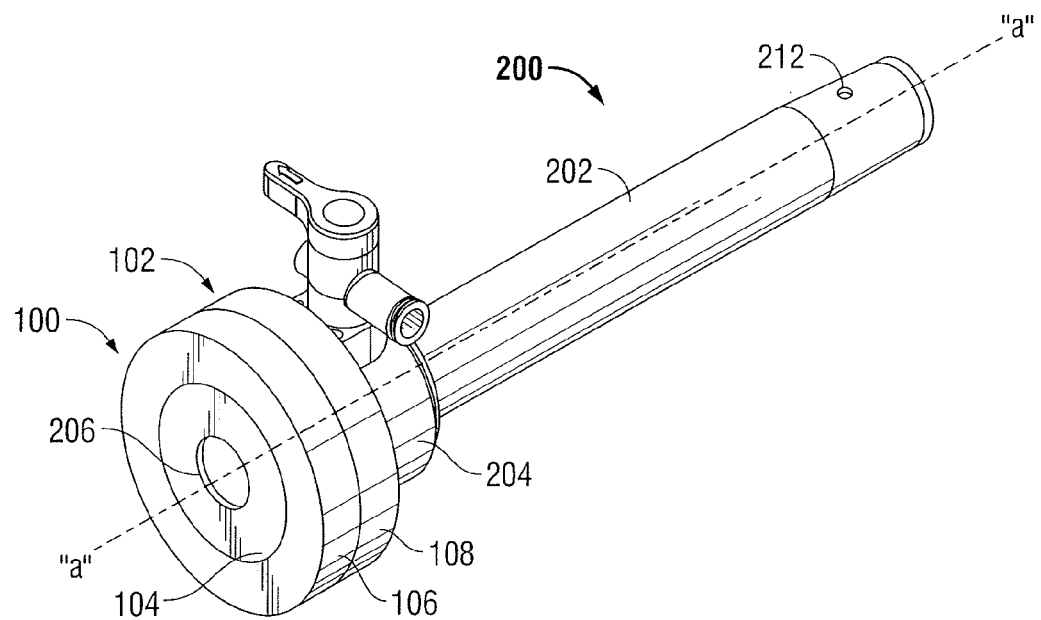
FIG. 2 is a left, perspective view of a trocar assembly and a seal assembly in accordance with the principles of the present disclosure.

Referring now to the drawings, in which like reference numerals identify identical or substantially similar parts throughout the several views, FIGS. 1-2 illustrate a seal assembly 100 in accordance with one embodiment of the present disclosure mounted to a trocar assembly 200. Trocar assembly 200 may be any conventional trocar suitable for the intended purpose of accessing a body cavity and permit introduction of instruments therethrough. Trocar assembly 200 is particularly adapted for use in laparoscopic surgery where the peritoneal cavity is insufflated with a suitable gas, e.g., $CO_2$, to raise the cavity wall from the internal organs therein. Trocar assembly 200 is typically used with an obturator assembly (not shown) which is a sharp pointed instrument positionable within the passageway of the trocar assembly 200. The obturator assembly is utilized to penetrate the abdominal wall and then is subsequently removed from the trocar assembly 200 to permit introduction of the surgical instrumentation utilized to perform the procedure.

With reference to FIGS. 1-2, trocar assembly 200 includes trocar sleeve 202 and trocar housing 204 mounted to an end of the sleeve 202. Any means for mounting trocar sleeve 202 to trocar housing 204 are envisioned including threaded arrangements, bayonet coupling, snap-fit arrangements, adhesives, etc. Trocar sleeve 202 and trocar housing 204 may also be integrally formed. Trocar sleeve 202 defines a longitudinal axis "a-a" extending along the length of sleeve trocar 202. Trocar sleeve 202 further includes an internal longitudinal passage 206, defined therein and dimensioned to permit passage of surgical instrumentation, therethrough. An aperture 212 is defined adjacent the distal end of trocar sleeve 202, which extends through the wall of the trocar sleeve 202. In the following description, as is traditional the term "proximal" refers to the portion of the instrument closest to the operator while the term "distal" refers to the portion of the instrument remote from the operator.

Aperture 212 permits passage of insufflation gases through trocar sleeve 202 during the surgical procedure. Trocar sleeve 202 may be formed of stainless steel or other rigid materials such as a polymeric material (or the like) and may be clear or opaque depending upon a particular purpose. The diameter of trocar sleeve 202 may vary, but, typically ranges from about 10 mm to about 15 mm for use with the seal assembly 100 of the present disclosure. Trocar housing 204 includes a port opening 214 defined therein, which is configured to receive luer fitting 216 therein (See FIGS. 1, 2, and 4). Luer fitting 216 is adapted for connection to a supply of insufflation gas and incorporates valve 218, which selectively opens and closes the passage of the luer fitting 216 to regulate the flow of insufflation gas into the peritoneal cavity.

With continued reference to FIGS. 1-4, seal assembly 100 will be discussed in detail. Seal assembly 100 may be a separate component from trocar assembly 200 and, accordingly, may be adapted for releasable connection to the trocar assembly 200. Alternatively, seal assembly 100 may be integrally incorporated as part of trocar assembly 200 forming a single unit. Seal assembly 100 includes a seal housing, having a piston seal 104 disposed therein. Seal housing 102 is generally dimensioned to house the various internal cooperating components of the sealing assembly 100. Seal housing 102 also defines central seal housing axis "b-b" which is preferably parallel to the axis "a-a" of trocar sleeve 202 and, more specifically, coincident with the axis "a-a" of the trocar sleeve 202. Seal housing 102 incorporates two housing components, namely, first and second housing components 106 and 108, respectively, which, when assembled, form the seal housing 102.

Figures 4, 5:
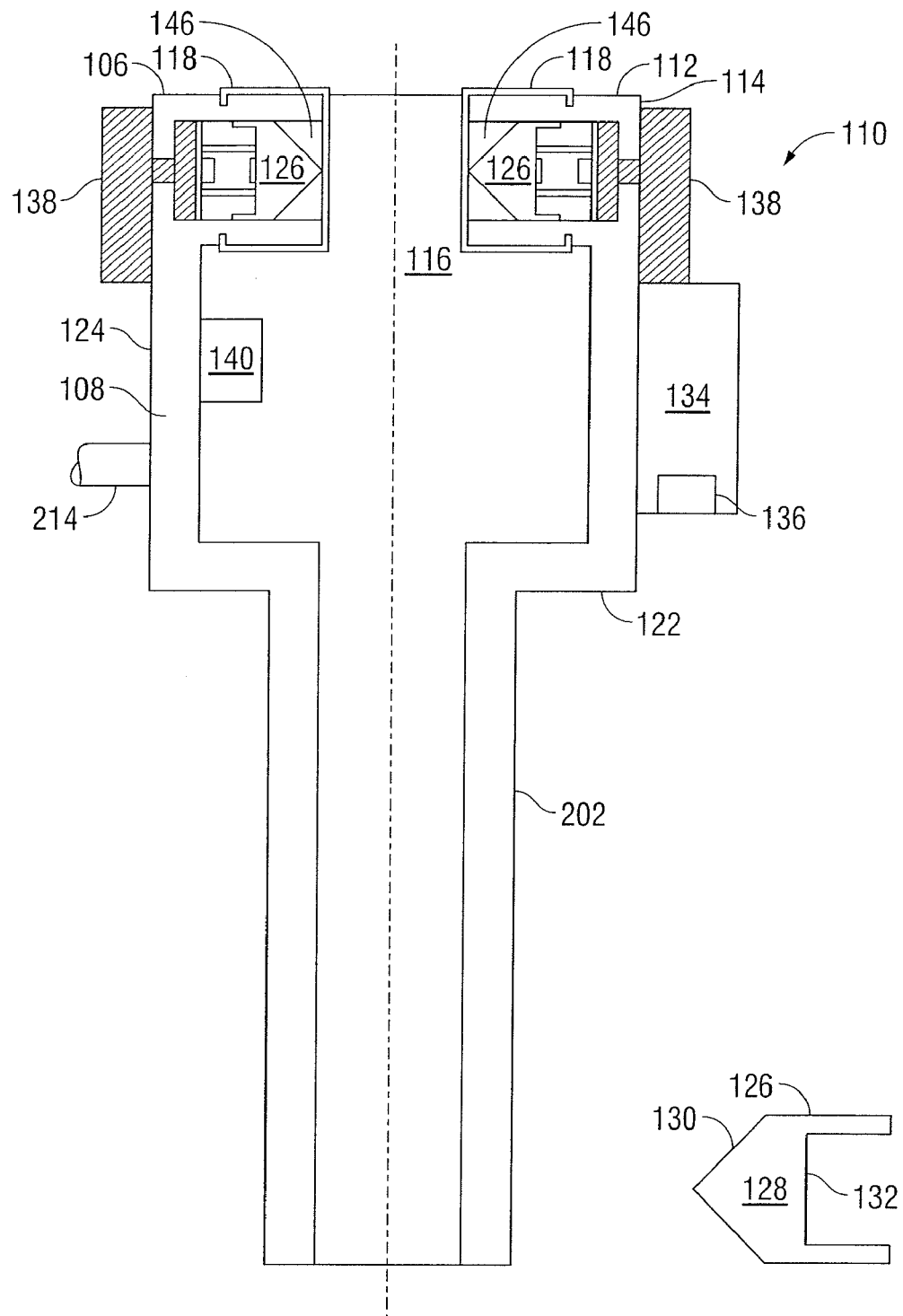
FIG. 4 is a side, cross-sectional view of a trocar and seal assemblies in accordance with the present disclosure.
FIG. 5 is a side, cross-sectional view of a piston member for use with the trocar and seal assemblies in accordance with the embodiment of FIGS. 1-4.
Figure 6:
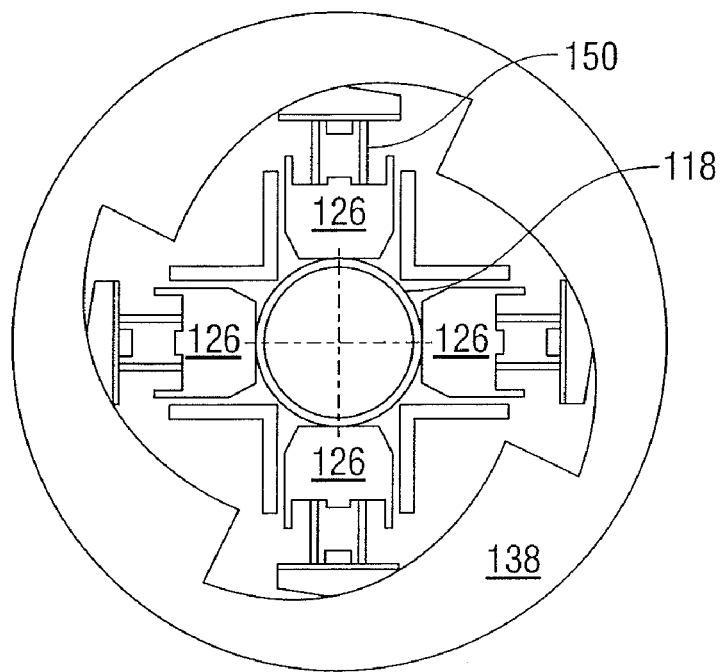
FIG. 6 is a top, partial internal view of the trocar and seal assemblies in accordance with the embodiment of FIG. 4.
Figure 7:
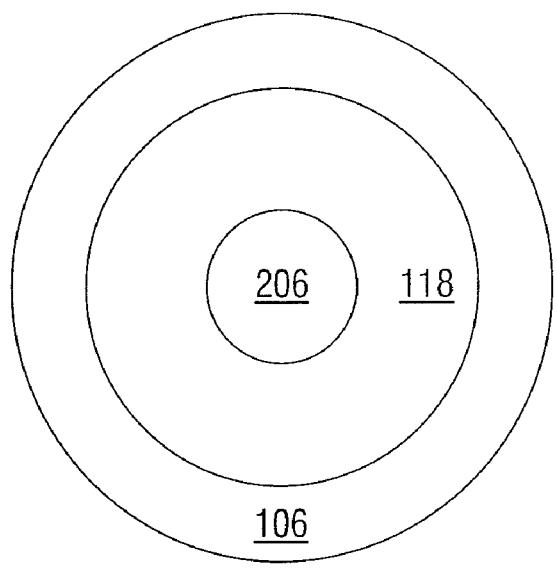
FIG. 7 is a top view in accordance with the embodiment of FIG. 4.

As shown in FIG. 4, first housing component 106 defines inner or proximal guide wall 112 and outer cylindrical wall 114, disposed radially outwardly therefrom. Proximal guide wall 112 defines a central passage 116, which is configured to laterally confine an instrument (not shown) within the seal housing 102. Proximal guide wall 112 further includes a flexible seal member 118 moveably disposed thereon and positioned to automatically engage an outer shaft or a surgical instrument upon insertion into central passage 116 as explained in more detail below. Outer wall 114 surrounds proximal guide wall 112 and extends distally therefrom.

Second housing component 108 of the seal housing 102 includes a transverse wall 122 and a cylindrical portion 124. Cylindrical portion 124 is dimensioned to mate with the outer wall 114 of first housing component 106, as best shown in FIG. 2.

Figure 3:
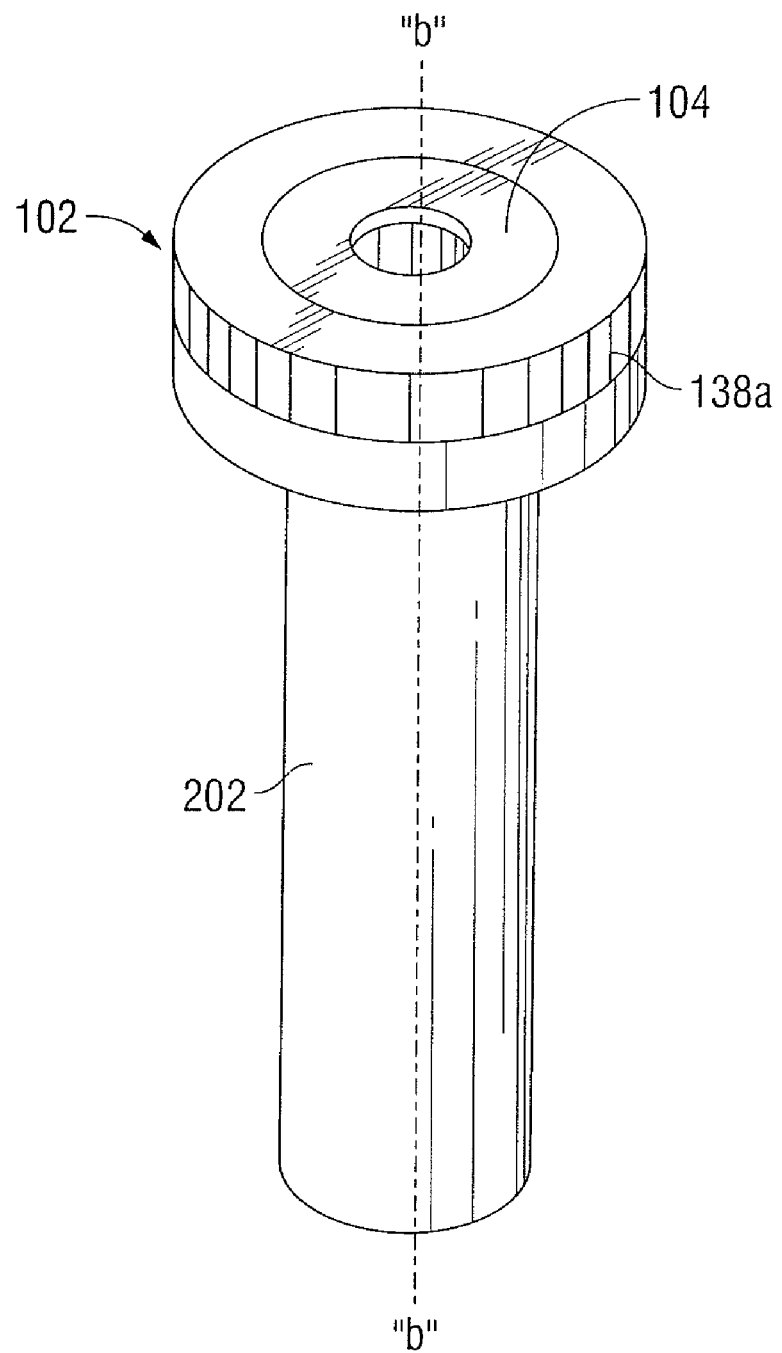
FIG. 3 is rear, perspective view of a trocar assembly and a seal assembly in accordance with the embodiment of FIGS. 1-2.

Referring now to FIGS. 3-5, a piston seal 104 is mounted between the first housing component 106 and second housing component 108. The assembled components are held together by a series of screws or other, positive fastening means extending through circumferentially-disposed holes. Piston seal 104 includes a plurality of piston members 126 each including a piston body 128, a tapered leading edge 130, and an aft end 132. (See FIG. 5) The plurality of piston members 126 are anchored within the seal housing 102, in a series of channels 146 that surround the periphery of the central passage 116. As the plurality of piston members 126 are actuated, a force is applied to the outer most end of each of the plurality of piston members 126 causing each of the plurality of pistons members 126 to move within the channels 146. The movement of the plurality of seal members 126 forces the seal member 118 to move between a first relative position and a second relative position.

Flexible seal member 118 may be fabricated from a single suitable elastomeric material having sufficient resiliency to stretch and form a seal about an inserted objected. Suitable materials include, but are not limited to polyurethane and copolyester. To minimize friction the elastomeric materials may be coated with silicon, the product polytetrafluoroethylene sold under the trademark TEFLON®, or the like.

The plurality of piston members 126 may be fabricated from any rigid material, including but not limited to plastic, metal, or composite. The plurality of piston members 126 may also be fabricated from a variety of different materials, e.g., the piston body 128 being made from a plastic material and the tapered leading edge 130 being made from a composite material. To minimize friction, the plurality of piston members 126 and/or channels 146 may be made from or coated with a low friction material.

Prior to the insertion of a surgical instrument, the piston seal 104 is biased in an open orientation with the seal assembly 100 resting in a first position relevant to the proximal guide wall 112. Upon the insertion of a surgical instrument, the plurality of piston members 126 automatically moves from the first position to a second position relative to the proximal guide wall 112. The plurality of piston members are substantially closer to one another. The plurality of piston members 126 move automatically and, preferably, simultaneous, to encapsulate and engage the outer shaft of the surgical instrument and form a seal therearound. Instruments of varying diameters may be selectively inserted and withdrawn from the trocar without interrupting or compromising the integrity of the surgical cavity. The relative size and dimension of the central passage 116 automatically adjusts and regulates to adapt to surgical instrumentation of various sizes.

The actuation mechanism 110 moves the piston seal 104 between the first relative, or open position, and the second relative position engaging the surgical instrument to establish a sealing relation therewith or to close the piston seal 104. The actuation mechanism 110 may include a motor 134 (See FIG. 4) having an associated switch 140, which regulates the operation of the plurality of piston members 126 the switch 140 may be an "on/off" switch, which (when placed in the "on" position) configures the piston seal 104 for automatic engagement of a surgical instrument's shaft. The motor 134 may be any suitable miniature electric motor which may be battery powered. The motor output is operatively connected to the plurality of piston members 126 of piston seal 104 in a manner to effect linear movement of the piston members 126 between the first and second relative positions. Various electrical connections for connecting the plurality of piston members 126 to the motor 134 are envisioned and appreciated by one skilled in the art.

The force on the outer shaft of the surgical instrumentation may be applied by one or more resilient springs 150. The springs 150 may be configured to extend relative to proximal guide wall 112 at different distances to accommodate off-center insertion or movement of the surgical instrument within the surgical cavity, e.g., some of the plurality of piston members 126 may travel a greater distance within channel 146 than some of the other plurality of piston members 126 relative to a respective proximal guide wall 112. In this instance, some of the plurality of piston members 126 react against the surgical instrument without much travel while some of the plurality of piston members 126 are allowed to travel greater distances in order to contact the surgical instrument. The resilient springs 150 also act as guides to keep the plurality of pistons members 126 properly aligned.

The motor 134 may also be controlled by the interaction between the surgical instrumentation and a switch 140. As the inserted instrument contacts the switch 140, the switch 140 is triggered and activates the motor 134. The motor 134, in turn, applies a force via the actuation mechanism 110 to the plurality of piston members 126. For example, in one embodiment, a motor 134 acts upon the ramp member 138 to cause ramp member 138 to rotate in a given direction. As the ramp member 138 rotates, the force from the motor 134 is translated through the resilient spring 128 to the piston members 126, causing the plurality of piston members 126 to move between relative positions. As ramp member 138 rotates clockwise the piston seal 104 closes and when the ramp member 138 rotates counterclockwise the piston seal 104 opens. Ramp member 138 may include a scalloped or textured outer surface 138*a* (See FIG. 3), which is dimensioned for a gripping engagement by the user to facilitate rotation.

A sensor 152 may be employed in place of a switch to regulate and control the movement of the plurality of piston members 126 for engaging and disengaging the surgical instrumentation. The sensor 152 is typically located at a position that is distal to the piston seal 104 within the seal housing 102 such that as the surgical instrument is introduced into the center passage 116, the surgical instrument engages the sensor 152. Once engaged, the sensor 152 activates the motor 134 causing the piston seal 104 to constrict around the surgical instrument. Thus, the plurality of piston members 126 move from a first relative position to a second relative position. The sensor 152 may be configured to interact with a central process unit to determine which of the plurality of piston members 126 are actuated and the degree of actuation. Once the surgical instrument is removed from the central passage 116, sensor 152 reactivates and the plurality of piston members 126 reset back to the first position to allow the surgical instrument to be removed without damage to the piston seal or requiring substantial force and which maintains the integrity of the surgical cavity.

Resistive circuitry 136 may be utilized to determine the desired or acceptable load place upon the outer shaft of the surgical instrument by the plurality of piston members 126. For example, when the motor 134 operates, the motor 134 draws an electrical current that can be measured by resistive circuitry 136 associated with the motor 134. It is envisioned that other alternative uses of resistive circuitry may be implemented to measure the load upon the motor 134. Once a specific, predetermined load is detected by the resistive circuitry 136, the motor 134 stops, which in turn stops the plurality of piston members 126 in the second relative position and holds the plurality of piston members 126 against the instrument shaft.

Although a motor 134 is disclosed as part of the actuation mechanism 110, it is appreciated that the actuation mechanism 110 may be manually operated by a clinician. There are several ways a clinician can cause the linear movement of the plurality of piston members 126 and activate the piston seal 104. One way is to manually rotate the ramp member 138 by the scalloped outer surface 138a. Another alternative is a manual lever connected to an actuation mechanism reacting upon the pistons through various linkages (not shown).

Figure 8:
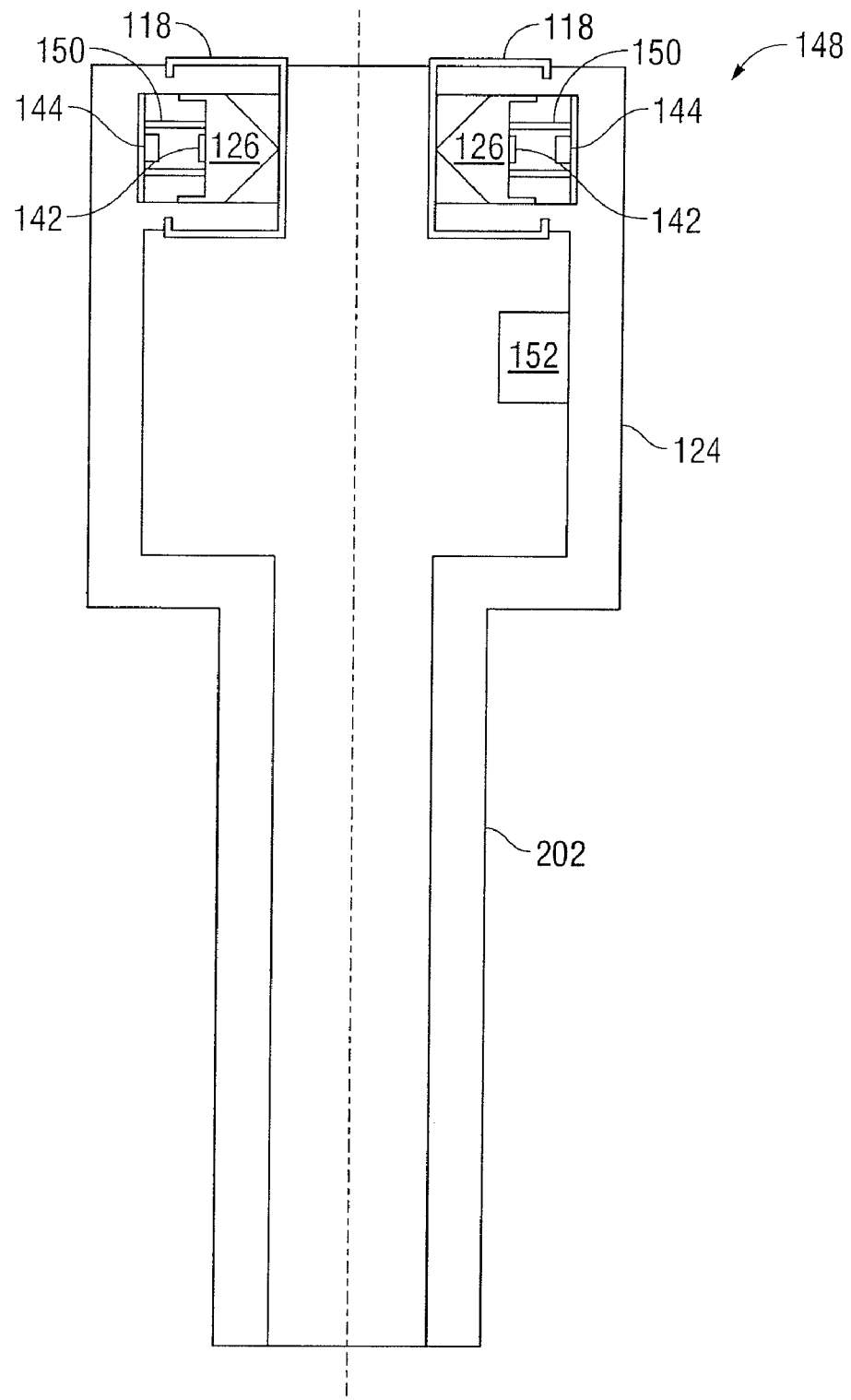
FIG. 8 is a side, cross-sectional view of the trocar and seal assemblies in accordance with the present disclosure.
Figure 9:
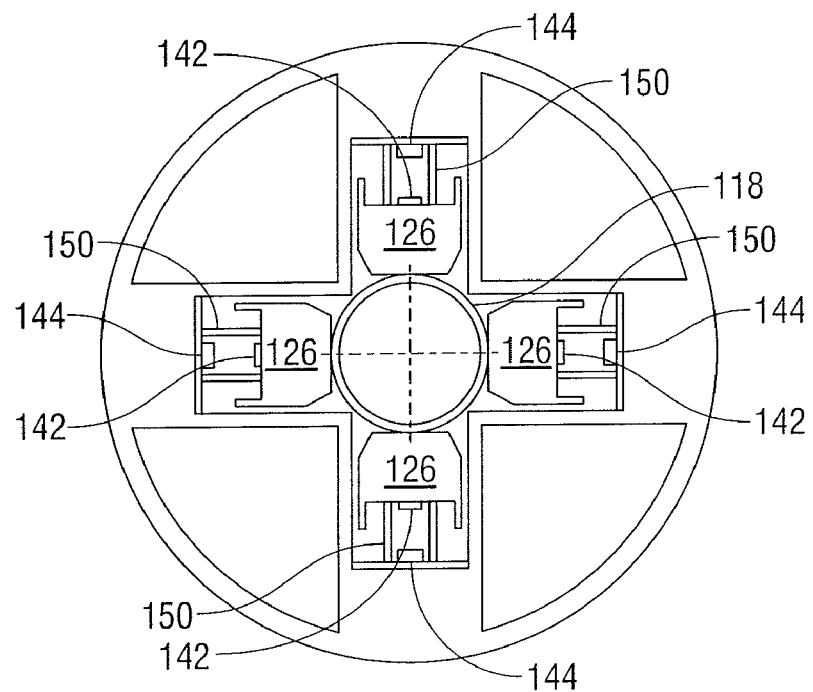
FIG. 9 is a top, internal view of the trocar and seal assemblies in accordance with the embodiment of FIG. 8.
Figure 10:
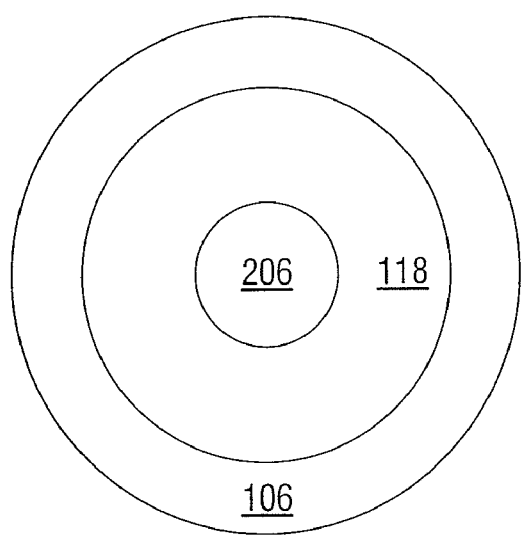
FIG. 10 is a top view in accordance with the embodiment of FIG. 8.
Figure 11:
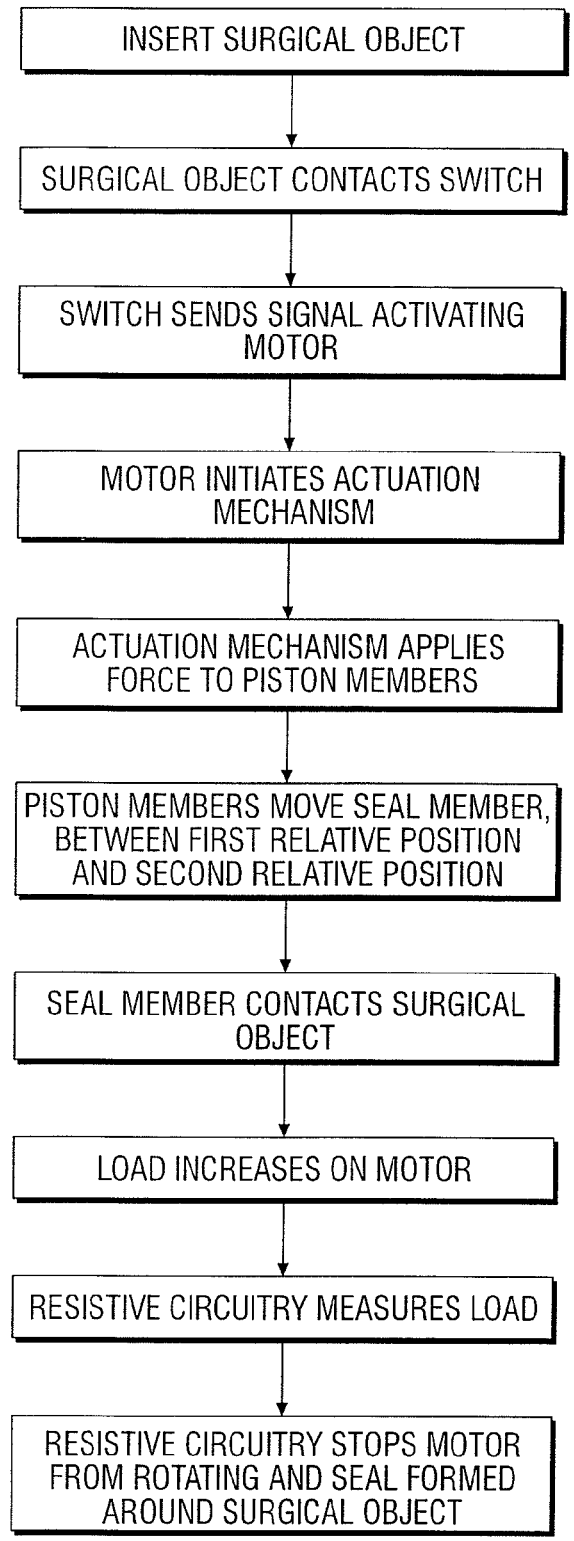
FIG. 11 is a flow chart illustrating one method of operation of the trocar assembly in accordance with the present disclosure.

In another embodiment, as shown in FIG. 8, the actuation mechanism 110 includes an electromagnetic repulsion system 148. In this instance, at least two magnets are used in each piston channel 146 a first magnet 142, having a first magnetic polarity, is attached to the piston member 126 and a second magnet 144 is attached to the wall 124 opposite the piston shaft end with a repelling magnetic polarity pointing towards the first magnetic polarity. As magnet 144 is electrically energized, magnet 142 is forced away from the wall 124, causing the piston seal 104 to move from the first relative position to the second relative position.

While the invention has been particularly shown, and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed:
1. A surgical portal apparatus, comprising:
 a housing;
 a portal member extending from the housing and having a longitudinal axis defined therethrough, the portal member dimensioned for positioning within tissue and defining an opening;
 a pliable seal having inner seal portions defining a seal passage for reception of a surgical instrument introduced within the opening, the inner seal portions dimensioned for establishing a substantial seal about the surgical instrument;
 a plurality piston members within the housing, the piston members being engageable with the inner seal portions of the seal defining the seal passage, and adapted for movement relative to the housing to cause corresponding movement of the inner seal portions and thereby control a dimension of the seal passage; and,
 a motor operatively coupled to the piston members and actuable to move the piston members.

2. A surgical portal apparatus as defined in claim 1, further comprising:
 a plurality of channels defined within the housing, each channel dimensioned and adapted to accommodate a corresponding piston member, the channels being configured to restrict movement of the pistons in a radial direction.

3. A surgical portal apparatus as defined in claim 1, wherein the piston members are dimensioned and adapted to move independently relative to one another.

4. A surgical portal apparatus as defined in claim 1, including resistive circuitry associated with the motor and being adapted to detect an increased load on the motor to thereby releasable secure the motor in an actuated orientation.

5. A surgical portal apparatus as defined in claim 1, further comprising:
 at least one sensor positioned within the housing, the sensor adapted to measure the size and location of the surgical object during introduction of the surgical object within the passage of the housing, to the senor operable coupled to the actuation mechanism to regulate the movement of the plurality of piston members based on information from the sensor.

6. A surgical portal apparatus as defined in claim 1, wherein the pliable seal includes a proximal seal face and a distal seal face, and defines a channel between the proximal seal face and the distal seal face, the channel at least partially accommodating the piston member.

7. A surgical portal apparatus as defined in claim 6, wherein the piston members are adapted for radial movement within the channel and relative to the longitudinal axis between a first unactuated position and a second actuated position.

8. A surgical portal apparatus as defined in claim 7, including a switch operatively connected to the motor, the switch being actuable to actuate the motor.

9. A surgical portal apparatus as defined in claim 7, wherein the switch is dimensioned and adapted to be manually actuated.

10. A surgical portal apparatus as defined in claim 7, wherein the switch is dimensioned and positioned to be engaged by the surgical instrument upon introduction within the opening of the portal member.

11. A surgical portal apparatus as defined in claim 1, wherein the inner seal portions are dimensioned to interconnect the proximal seal face and the distal seal face.

12. A surgical portal apparatus as defined in claim 1, including a sensor positioned to detect at least one of a dimension or location of the surgical object to control operation of the motor to thereby regulate movement of the piston members.

13. A surgical portal apparatus as defined in claim 12, wherein the resistive circuitry is adapted to stop operation of the motor upon detection of a predetermined load thereon wherein the piston members are secured in the second actuated position.

14. A surgical portal apparatus as defined in claim 1, including resistance circuitry associated with the motor and adapted for detection an increased load on the motor to thereby control operation of the motor.

15. A surgical portal apparatus, comprising:
 a housing;
 a portal member extending from the housing, the housing and the portal member defining a longitudinal axis and having a longitudinal passageway for reception of a surgical object within tissue;
 a single pliable seal having inner portions defining a seal opening for reception of the surgical object in substantial sealed relation therewith;
 a plurality of piston members within the housing, the piston members being adapted for at least radial movement from a first initial position to a second actuated position to move the inner seal portions defining the seal opening in a radial inward direction to reduce a dimension of the seal opening;
 an actuation mechanism operatively connected to the piston members and being actuable to cause movement of the piston members towards the second actuated positions; and a sensor operatively coupled to the actuation mechanism and adapted to detect one of dimension or location of the surgical object, and cooperate with the actuation mechanism to control movement of the piston members between the first initial and second actuated positions.

16. A surgical portal apparatus as defined in claim 15, wherein the actuation mechanism includes an electromagnetic repulsion system for actuating the plurality of piston members.

* * * * *